United States Patent [19]

Griparis

[11] 4,206,774
[45] Jun. 10, 1980

[54] DENTAL FLOSSER

[76] Inventor: Andrew G. Griparis, 251 Republic Ave., Joliet, Ill. 60435

[21] Appl. No.: 929,875

[22] Filed: Jul. 31, 1978

[51] Int. Cl.² ............................................. A61C 15/00
[52] U.S. Cl. .................................................. 132/92 R
[58] Field of Search .............. 132/92 R, 91, 93, 92 A; 32/40

[56] References Cited

U.S. PATENT DOCUMENTS

| | | | |
|---|---|---|---|
| 1,468,942 | 9/1923 | Gamble | 132/92 R |
| 1,723,842 | 8/1929 | Cammack | 132/92 R |
| 1,952,358 | 3/1934 | Bohm | 132/92 R |
| 2,113,439 | 4/1938 | Bean | 132/92 R |
| 2,460,591 | 2/1949 | Luzar | 132/92 R |
| 2,516,539 | 7/1950 | Atols | 132/92 R |
| 3,667,483 | 6/1973 | McCabe | 132/92 |
| 3,759,274 | 9/1973 | Warner | 132/92 R |
| 3,828,804 | 8/1974 | Ely | 132/91 |
| 3,847,167 | 11/1974 | O'Brien | 132/92 R |
| 4,022,229 | 5/1977 | Minka | 132/92 R |

FOREIGN PATENT DOCUMENTS 735125 8/1932 France ..................... 132/91

*Primary Examiner*—Jay N. Eskovitz
*Attorney, Agent, or Firm*—Ernest S. Kettelson

[57] ABSTRACT

A dental flosser comprising an elongated handle having a storage chamber for a spool of dental floss and a forked head having two spaced apart arms secured to one end of the handle. A through passageway is provided from the storage chamber in the handle to the forked head to feed a strand of dental floss from the chamber onto and around the outer ends of the arms of the forked head. The connection of the head to the handle includes means to capture and hold the adjacent portion of the strand of dental floss securely when tightened. The outwardly extending length of dental floss is then drawn taut across the span between the outer ends of the spaced apart arms of the forked head, and the free end portion is secured by winding around a circular wedge member. A cutting assembly is provided adjacent the wedge member to enable cutting off the excess portion of the dental strand. The flosser is then ready for use. A fresh strand of dental floss can be provided across the spaced apart arms of the forked head by loosening the connection between the handle and head, drawing a new length of dental floss outwardly from the storage chamber, tightening the head and handle connection, positioning the new strand around and across the spaced apart arms, wedging the end portion, and cutting off the excess by means of the adjacent cutting assembly.

3 Claims, 9 Drawing Figures

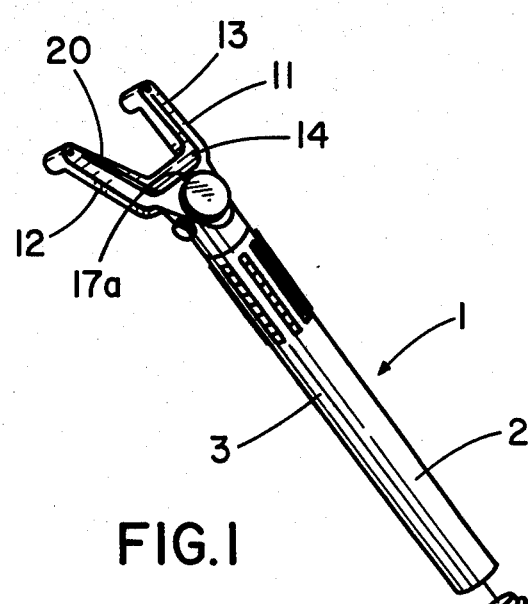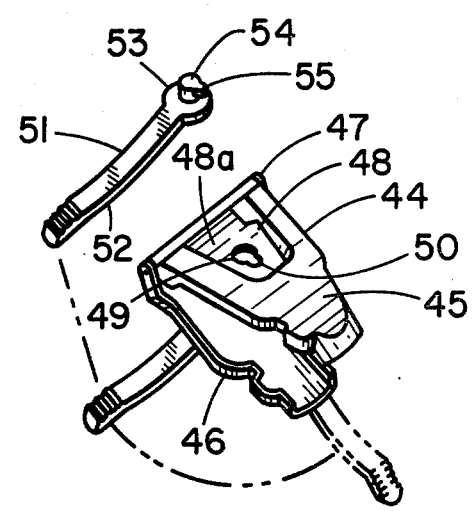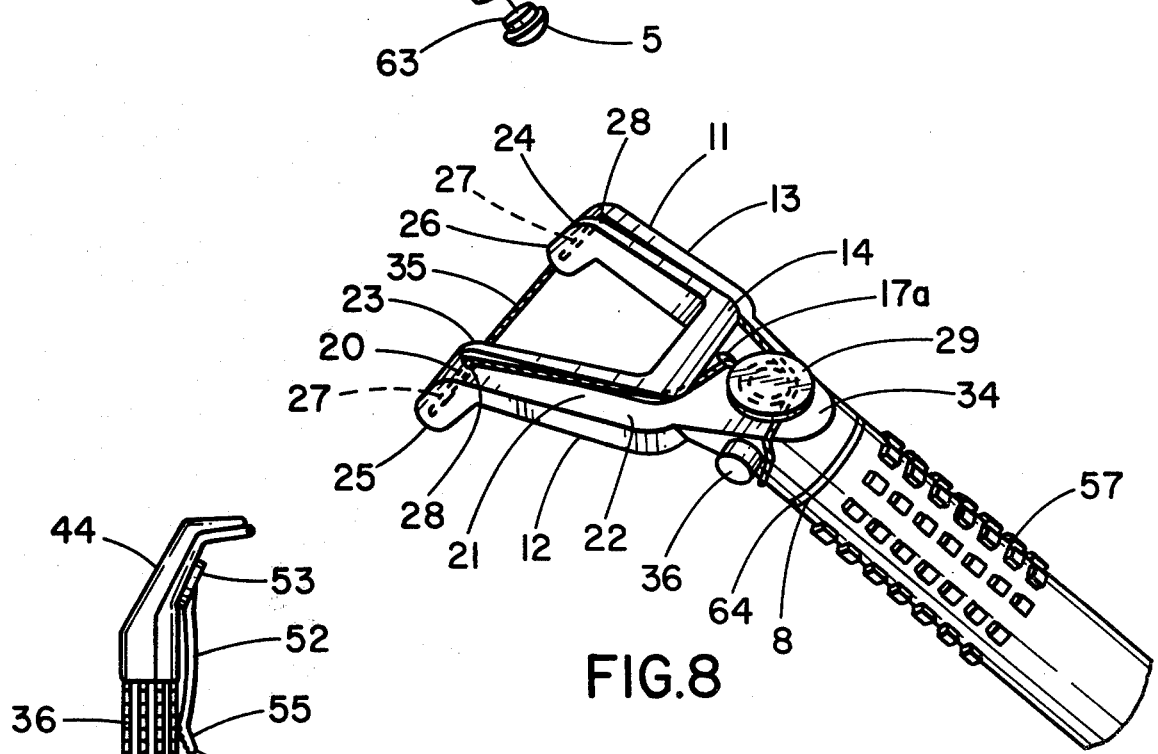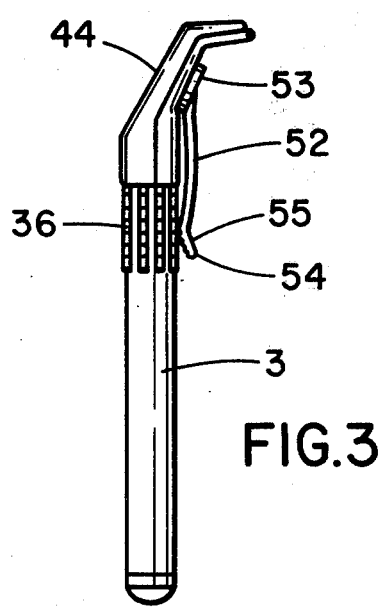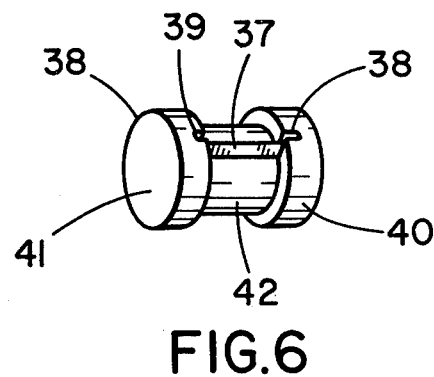

DENTAL FLOSSER

BACKGROUND OF THE INVENTION

This invention relates to the field of dental flossing devices in which a holder carries a strand of dental floss positioned for use in cleaning between the teeth.

Various types of holders and frames have been devised for holding strands of dental floss for cleaning teeth. In some of these, a length of dental floss is simply affixed to one anchor point and stretched across an open span and affixed to a spaced apart anchor point, without any provision for supplying a new length of dental floss after the first length has been used. Such devices require cutting separate lengths of floss from a separate supply source each time that a new length of dental floss is required.

Another way of using dental floss known to the prior art is simply for the dentist, or dental assistant, or other user, to grasp opposite ends of a length of dental floss in each hand and manipulate the floss back and forth between a patient's teeth manually.

Various types of mechanized flossers have also been attempted and are known to the prior art. However, it has been found that mechanized flossers which move the dental floss back and forth rapidly between the teeth can cause damage to the gums. The vibratory or reciprocating movement provided by an electric motor or vibrator is too vigorous for safe use and proper care.

The nature of dental floss makes it difficult to grasp securely and to hold a tensioned strand securely by mechanical means. It is also difficult to provide a storage chamber or reservoir in a mechanical flossing device from which a continuous supply of dental floss can be readily withdrawn as each succeeding length is used. The present invention is devised to overcome these problems faced by the prior art.

SUMMARY OF THE INVENTION

It is an object of the invention to provide a dental flosser having a storage chamber for providing a continuous supply of dental floss as succeeding lengths are used.

It is an object of the invention to provide a dental flosser having a forked end portion in which a length of dental floss is secured at a point outwardly of each arm of the fork enabling a tensioned strand to be carried across the span between two arms of the fork.

It is an object of the invention to provide dental flosser having a tubular body portion, a cavity therein for receiving a supply of dental floss, a closure cap at one end, a frusto-conical projection extending from the opposite end, an outlet aperture adjacent said frusto-conical projection through which a strand of dental floss may be drawn, a forked head portion including two arms projecting outwardly in spaced apart relation from a base portion of said forked head, a recess in said head having a corresponding frusto-conical projection configuration for seating therein of the frusto-conical projection of the tubular body portion, an aperture through the base portion of said head opening to said frusto-conical recess to receive therethrough a strand of dental floss for wrapping around the outer ends of the spaced apart arms of the forked end, the dental floss being captured and held securely between the corresponding faces of the frusto-conical projection and frusto-conical recess when the head is tightened against the tubular body portion of the recess.

It is an object of the invention to provide a dental flosser having a forked head portion, a wedge member for securing an end portion of a strand of dental floss which has been drawn tightly across the span between two extending arms of said forked head portion.

It is an object of the invention to provide a dental flosser having a cutting device positioned on the body portion thereof and in which the cutting device is protected from accidental contact by a user.

BRIEF DESCRIPTION OF THE DRAWINGS

FIG. 1 is a perspective view of a dental flosser in accordance of this invention.

FIG. 2 is a perspective view of a sanitary cover for a dental flosser in accordance with this invention.

FIG. 3 is a side elevation view of a dental flosser in accordance with this invention having the sanitary cover shown in FIG. 2 affixed thereon.

FIG. 6 is an enlarged perspective view of the cutting device incorporated in the head of the dental flosser of this invention.

FIG. 8 is an enlarged perspective view of a dental flosser in accordance with this invention with portions of the passageway in the head and forked arms shown in phantom.

DESCRIPTION OF PREFERRED EMBODIMENT

Figure 4:
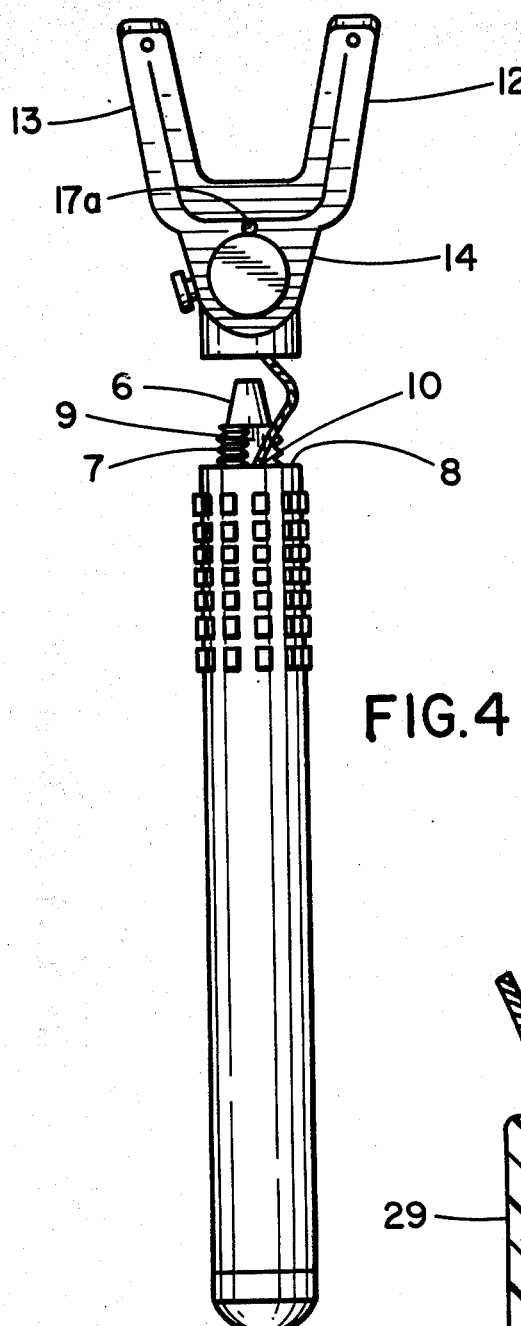
FIG. 4 is a front elevation, partially exploded view of a dental flosser in accordance with this invention showing the forked head separated from the tubular body portion.

A dental flosser 1, includes a tubular body portion 2, having a circular outer wall 3, and a cylindrical cavity or storage chamber 4. A closure cap 5 is provided to close one end of cylindrical storage chamber 4. At the opposite end of the tubular body portion 2, a frusto-conical projection 6 extends outwardly having an externally threaded section 7 at the base thereof. The externally threaded section 7 is of smaller diameter than the outer wall 3 of the tubular body portion 2 with an annular shoulder 8 extending from the edge of the outer wall 3 to the threaded section 7. A flat face portion 9 is formed along one side of threaded section 7 for a purpose to be described subsequently herein. A small aperture 10 is formed through the shoulder 8, adjacent to the bottom portion of flat 9, and opening into the cylindrical storage chamber 4.

The dental flosser includes a forked head 11, having two spaced apart arms 12 and 13 projecting outwardly from a base portion 14. A recess 15 is formed in the base portion of the forked head 11, said recess having inner walls of frusto-conical configuration corresponding to the configuration and dimension of the frusto-conical projection 6 of the body portion 2. The recess 15 includes an internally threaded section 16 corresponding to the externally threaded section 7 of the body portion 2 for threaded engagement therewith when the forked head 11 is secured to the body portion 2. The forked end portion includes a small channel 17 extending from the inner end of recess 15 through the base 14, and opening to the outer wall of base 14 through aperture 17a at a point between the arms 12 and 13 of the forked head 11.

A spool 18 of dental floss is inserted in storage chamber 4 of body portion 2. One end 19 of the spool of dental floss 18 is drawn through the aperture 10 opening through the shoulder 8 of the body portion 2 and then along the flat face 9 of the threaded section 7. When the head 11 is screwed on to the body portion 2 with externally threaded section 7 threadedly engaged with internally threaded section 16 of the recess 15 of the head 11, it will be seen that the flat face 9 provides space for the strand of dental floss to pass from aperture 10 into recess 15. The end 19 of dental floss is then drawn through the small channel or passageway 17 and out through aperture 17a.

A positioning passageway 20 is formed in the arms 12 and 13 of forked end 11 to receive the strand of dental floss 18 and position it for use. Such positioning passageway 20 includes groove 21 formed around the rear face 22 of the head 11, such groove 21 extending from the outer end 23 of forked arm 12 and continuing inwardly thereof toward the base 14, around the base and then continuing outwardly along forked arm 13 toward its outer end 24. The groove 21 opens to the outwardly facing side of arms 12 and 13.

The forked arms 12 and 13 each include angled projections 25 and 26 respectively extending from their free ends. A small channel 27 is formed through each of the angled projections 25 and 26 opening to the free ends thereof and have apertures 28 opening at the opposite or inward end of said channels 27 at a location adjacent the outer ends of groove 21 where groove 21 terminates in arms 12 and 13 respectively.

The end 19 of the strand of dental floss 18 is drawn from aperture 17a in the base 14 of forked end 11 into groove 21 along the forked leg 12, then inserted into the channel 27 which extends through the angled projection 25 of forked leg 12. The end 19 of dental floss 18 is then drawn across the span between the outer end 23 of arm 12 into outer end 24 of arm 13 and inserted into the channel 27 of angled projection 26 of forked arm 13. The end 19 of dental floss 18 is pushed through channel 27 until it projects through the aperture 28 of forked arm 13, whereupon it is seated in the portion of groove 21 which extends along forked arm 13. The end 19 of dental floss 18 is drawn inwardly along groove 21 until it reaches circular wedge member 29 which is positioned on the outer wall of base 14 of forked head 11. The circular wedge member 29 includes a sloping annular wall 30 which tapers inwardly from outer edge 31 to inner edge 32 which forms an annular apex 33 with the outer wall 34 of base portion 14 of forked head 11.

When the end 19 of dental floss 18 is drawn into proximity with the circular wedge member 29, a sufficient length is drawn past wedge member 29 to enable wrapping the strand of dental floss around such circular wedge member. The end 19 of dental floss 18 is then moved in a direction to draw the strand of dental floss tightly toward annular apex 33 around its entire circumference thereby wedging the strand of dental floss between the surface of wall 34 and sloping annular wall 30 of circular wedge member 29.

Before threading the strand of dental floss around the positioning passageway 20 of forked head 11, a sufficient length of dental floss 18 is drawn through the aperture 17a in the base 14 of forked end 11 which will reach around the positioning passageway 20 with enough of the strand remaining to wedge around the circular wedge member 29. When such sufficient length of dental floss has been drawn through aperture 17a, the forked head 11 is then screwed tightly against shoulder 8 of body portion 2 at which time the outer wall of frusto-conical projection 6 seats tightly against the correspondingly shaped frusto-conical inner wall of recess 15. This tightly captures that portion of the strand of dental floss 18 adjacent thereto between the inner wall of the recess 15 and the outer wall of frusto-conical projection 6. The strand of dental floss is then threaded through and around the positioning passageway 20 until the end 19 is drawn into proximity of circular wedge member 29 whereupon the strand is drawn tightly providing a tensioned strand portion 35 extending across the span from 12 to arm 13. The end 19 of dental floss 18 is then drawn around circular wedge member 29 as described above wedging that portion of the strand therein maintaining the tension on strand portion 35 for use in cleaning teeth.

A cutting assembly 36 is mounted along a portion of wall 34 adjacent to circular wedge member 29 to enable cutting off the excess portion of the strand of dental floss. Cutting assembly 36 includes a cutting knife 37 seated in grooves 38 and 39 formed in spaced apart annular members 40 and 41. A cylindrical post 42 extends between the annular members 40 and 41 and provides a support base for an edge of cutting knife 37. The cylindrical post 42 is of smaller diameter than annular end members 40 and 41. One of the annular members 40, is inserted into an undercut annular recess 43, having a dimension and configuration corresponding to that of annular member 40, formed in the base portion 14 of forked head 11. The forked head 11 and the annular member 40 of the cutting assembly 36 may be made of pliable material such as plastic or rubber so the annular member 40 may be pressed into the corresponding recess 43. The cylindrical post 42, and cutting knife 37, have a longitudinal dimension only long enough to project a small distance from the wall 34 of the base 14 of forked head 11 when the annular end member 40 has been seated in recess 43. At such time, the other annular end member 41 of the cutting assembly 36 faces outwardly of wall 34, and being of larger diameter than cylindrical post 42, it provides a protective shield around the entire circumference of cylindrical post 42. The cutting knife 37 has a short lateral dimension and extends outwardly from the annular wall of cylindrical post 42 only a short distance, only far enough to enable engagement therewith of the strand of dental floss and to enable cutting thereof when looped around and drawn firmly against the cutting edge.

A sanitary cover 44 is provided for the head 11 to protect it against external contamination when not in use. The sanitary cover 44 includes a pair of cover members 45 and 46 hinged together at one end by hinge pin 47. Cover member 45 includes a recess 48 having a base 48a in which an aperture 49 is formed. A corresponding aperture 49 is also provided in cover member 46. A slot 50 extends from one edge portion of apertures 49. A closure handle 51 is provided to secure the sanitary cover 44 in closed position after it has been attached to the head 11. Closure handle 51 includes an extended arm 52 and a circular head 53. A circular lug 54 projects axially from the circular head 53. A projecting detent member 55 extends laterally from the outer edge of projecting lug 54, the detent member 55 extending parallel to the face of circular head 53 and being spaced apart from the face of circular head 53 a distance which is sufficient to maintain the hinged cover members 45 and 46 in closed position after the projecting lug 54 has been inserted through apertures 49 in the hinged cover members 45 and 46 and rotated to a locking position. The projecting lug 54 of handle 51 is inserted through the apertures 49 of hinged cover members 45 and 46 with the detent member 55 aligned with slots 50 which open to apertures 49. After projecting lug 54 has been fully inserted so detent member 55 clears the base 48a of recess 48 in cover member 45, the handle 51 is rotated to a position in which the arm 52 extends in a direction normal to the hinge pin 47. At such point the arm 52 extends longitudinally along and adjacent to the wall 3 of tubular body portion 2. The arm 52 is preferrably curved from its end adjacent the circular head 53 in a direction which will bring the free end 54 of arm 52 into engagement with the wall 3 of tubular body portion 2 when the sanitary cover 44 is affixed to the head 11 of the dental flosser. The arm 52 also includes a short oppositely curved portion 55 at the free end 54. Such construction enables the arm 52 of closure handle 51 to serve as a pocket clasp whereby the dental flosser may be carried in the pocket of a dentist, dental technician or other user, and held securely therein.

The head 11 is formed in such a way that the forked arms 12 and 13 extend forwardly at an angle to a first plane through the axis of tubular body portion 2 which extends laterally in the direction in which the arms 12 and 13 are spaced apart. The forked arms 12 and 13 both project forwardly at the same angle to such plane. The forked arms 12 and 13 also extend laterally at an angle to a second plane through such axis which extends in a direction normal to said first plane. The angles formed by the lateral extension of each arm 12 and 13 are also equal but extend in opposite lateral directions from said second plane. The angled projections 25 and 26 extend forwardly at a slightly obtuse angle from the outer ends 23 and 24 of their respective arms 12 and 13. The length of the forked arms 12 and 13, their forwardly angled direction, plus the angled projections 25 and 26 across which tensioned strand 35 of dental floss 18 extends, provides a universal working position for such tensioned strand 35 out of the way of a user's hand which grasps the tubular body portion 2, and enabling universal rotational, lateral and longitudinal movement of the flosser when cleaning teeth.

Figure 5:
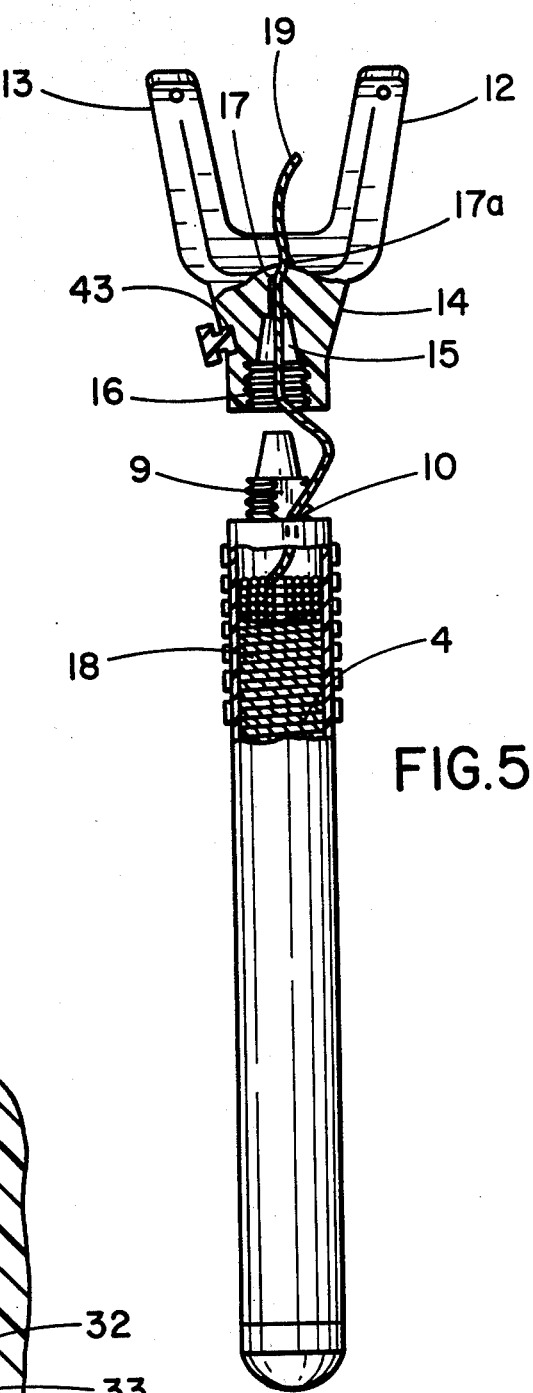
FIG. 5 is the same view as FIG. 4 but with portions of the head and body portion broken away to illustrate sections thereof.
Figure 7:
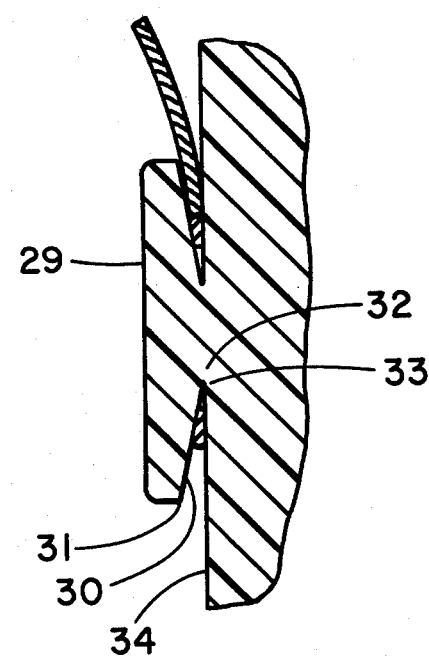
FIG. 7 is an enlarged sectional view through the circular wedge of the dental flosser in accordance with this invention.
Figure 9:
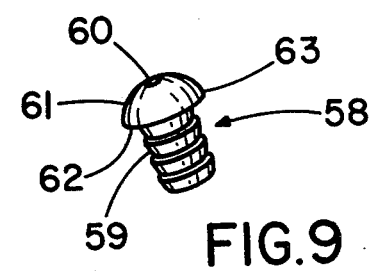
FIG. 9 is a perspective view of a sealing grommet for use in this invention.

In one modification of the dental flosser, as shown for exammple in FIGS. 1–5, the tubular body portion 2 includes a plurality of longitudinal ribs 56 extending in spaced apart relationship around the circumference of the outer wall 3 of tubular body portion 2 and from the area adjacent the forked head 11. The longitudinal ribs 56 provide friction increasing means for a user holding the tubular body portion 2 in his hand with the thumb and forefinger grasping the longitudinal rib portion. Such longitudinal ribs increase the frictional contact between the finger and thumb and the body of the flosser, particularly for rotational motion.

In the modification shown in FIG. 8 a plurality of longitudinal rows of short spaced apart lugs 57 are provided in lieu of the longitudinal ribs 56. The longitudinal rows of spaced apart lugs 57 provide friction increasing means for both rotational movement and reciprocal or longitudinal movement of the flosser when held in the hand of the user.

The longitudinal ribs 56 shown in FIGS. 1–5 are particularly adapted for use with a sanitary cover 44 of the type having a handle 51 shaped in such a way as to provide a pocket clasp as described above. The free end portions 54 and 55 of the handle arm 52 bear against adjacent ones of the longitudinal ribs 56 and enable both insertion and withdrawal of a portion of a pocket between the longitudinal ribs 56 and that portion of the handle arm 52 which bears thereagainst.

The dental floss may be inserted into the storage chamber 4 by helically winding on a spindle and then inserting into the chamber 4 whereupon the spindle may be withdrawn. The closure cap 5 is then affixed to close the insertion end of the storage chamber. One end 19 of the spool of dental floss must be threaded through the aperture 10 which extends through the shoulder 8 at the opposite end of the tubular body portion, and then threaded through channel 17 of the head 11 and around the forked arms 12 and 13 as described above.

To use the flosser, the head 11 is unscrewed slightly, causing the outer surface of the frusto-conical projection 6 to separate slightly from the inner surface of the corresponding frusto-conical recess 15. This provides a space for the strand of dental floss 18 to pass as it is drawn upwardly and around the forked arms 12 and 13. When a sufficient length of dental floss 18 has been drawn outwardly, the forked head 11 is rotated in the closing direction until it is screwed tightly against the shoulder 8 of tubular body portion 2 at which time the outer surface of frusto-conical projection 6 abuts tightly against the inner surface of the frusto-conical recess 15, thereby compressing the strand of dental floss 18 therebetween and holding it securely in place against further withdrawal. The free end 19 of dental floss 18 is then positioned in groove 21 of head 11, through passageway 27 in angled projection 25 of arm 12, across the span between the angled projections 25 and 26 of the forked arms 12 and 13, up through passageway 27 in angled projection 26 or arm 13, back into that portion of groove 21 which extends along forked arm 13. The end portion of the strand of dental floss is then wedged around circular wedge member 29 in the manner described above. The user has now positioned a tensioned length of dental floss 35 across the span between arms 12 and 13, which has been locked in place on each side of arms 12 and 13. The excess portion of the strand of dental floss after wedging around the circular wedge member 29 is brought into contact with the cutter assembly 36. The cutter assembly 36 is positioned on the wall 34 of head 11 in close proximity to the circular wedge member 29. The user then draws the excess strand of dental floss around the cylindrical post 42 of cutter assembly 36 and inside of the larger diameter annular end member 41. When the strand of dental floss is drawn tightly around the cylindrical post 42 of the cutter assembly 36 and brought into contact with the sharp edge of cutting assembly 36, the user can then cut the dental floss by tugging firmly on the excess portion thereby severing it from the strand of dental floss positioned for use in the flossing device.

The flossing device is then used manually, either by a user to clean his own teeth or by a dentist or dental assistant to clean the teeth of patients. The flossing device is manipulated manually by grasping the body portion between the thumb and the forefingers, with the thumb and forefinger in contact with the friction increasing ribs 56 or lugs 57, depending on the modification used.

After the tensioned strand 35 has been used and it is desired to provide a fresh strand of dental floss for use in the device, the forked head 11 is rotated slightly in the opening direction to loosen the grip on the strand of dental floss which has been held between the corresponding surfaces of the frusto-conical projection 6 and recess 15. The portion of the dental floss strand which has been wedged around the circular wedge member 29 is removed therefrom, and a new length of dental floss is then withdrawn from the storage chamber 4 by pulling at the free end until a fresh unused portion of dental floss appears across the span between the forked arms 12 and 13. The head is then again rotated in the tightening position to secure that portion of dental floss which is adjacent to the frusto-conical projection 6 and corresponding wall of recess 15 bearing tightly against each other. The other end of the fresh length of dental floss is secured around the circular wedge member 29, and the excess is again cut off by looping around the cutting assembly 36 and tugging thereon in the manner previously described.

A resilient sealing grommet or washer 58 is provided for seating in aperture 17a which opens to the outer wall 34 of the base portion 14 of forked head 11. The grommet or washer 58 may be made of pliable plastic material or of rubber, and it includes a slightly elongated cylindrical body portion 59 having a bore 60 extending therethrough. The diameter of bore 60 corresponds substantially to the diameter of the strand of dental floss used in the flosser, and is just sufficiently large enough to enable drawing the strand of floss through the bore 60 of washer 58 when seated in aperture 17a. The outer diameter of the cylindrical body portion 59 of sealing washer or grommet 58 corresponds substantially to the diameter of aperture 17a, and is sufficiently larger to require slight compression of the outer wall of cylindrical body portion 59 when inserted into aperture 17a. An annular head 61 is formed at the outwardly extending end of the sealing washer or grommet 58, the annular head 61 having a diameter larger than that of the cylindrical body portion. Annular head 61 includes a flat annular under-shoulder 62 extending outwardly from the cylindrical body portion to the peripheral edge 63 of annular head 61 and being substantially normal to said cylindrical body portion. The cylindrical body portion 59 of the sealing washer or grommet 58 is pressed into aperture 17a and inserted until the flat annular under-shoulder 62 abuts firmly against the portion of outer wall 34 which surrounds aperture 17a. The sealing washer or grommet 58 thus seals aperture 17a against entrance of water.

The junction of the base 14 of head 11 resting tightly against shoulder 8 of the tubular body portion 2 of the flosser when head 11 is screwed tightly in the closing direction also provides a water-tight seal.

The closure cap 5 includes a cylindrical wall portion 63 which has a diameter substantially corresponding to the diameter of storage chamber 4, and which is sufficiently large enough to provide a water-tight seal when inserted into chamber 4 from its open end to close the entrance thereto by the closure cap 5.

Thus, the storage chamber 4 in which the spool of dental floss 18 is stored is watertight when the head 11 is tightly secured to tubular body portion 2, when the closure cap 5 is in place, and when sealing washer or grommet 58 is mounted in place in aperture 17a. It is then possible to wash the flosser by simply placing under a running faucet, or by dropping into a basin of wash water, and washing until clean. The wash water is unable to penetrate into the floss storage chamber 4 from the aperture 17a, the juncture between the head 11 and body portion 2, or the end thereof fitted with closure cap 5.

The flosser in accordance with this invention may be made of a resilient plastic, rubber or other compressible material. The cylindrical wall portion 63 of closure cap 5 and the corresponding cylindrical wall 3 of tubular body portion 2 thus are mutually compressible against each other when closure cap 5 has been put in place to close the entrance to storage cavity 4. The same is true of the relationship between the sealing washer or grommet 58 when inserted in aperture 17a of the head 11 when the flosser is made of such resilient compressible material.

Other materials may be used for the head and body portions of the flosser, including metal and wood. In such case, the sealing washer or grommet 58 may be press fit into aperture 17a, and the cylindrical wall 63 of closure cap 5 may be similarly tightly fit into the open end of tubular body portion 2 to still provide a watertight seal at these points. A sealing washer 64 of rubber or other compressible material may be provided to seat on the shoulder 8 of the tubular body portion 2, to seal the juncture between the head 11 and the body portion 2 when tightened together.

I claim:

1. A dental flosser, comprising a body portion, a storage cavity therein to receive a supply of dental floss, a head portion secured to said body portion at a first end thereof, said head portion including spaced apart first and second positioning means to position a taut length of dental floss between said first and second positioning means, a communicating passageway from said storage cavity to said positioning means for a strand of dental floss to feed from said storage cavity to said positioning means, and tension retaining means to hold a said taut length of dental floss under tension between said first and second positioning means, wherein said tension retaining means includes first tension retaining means between said storage cavity and said first positioning means, and second tension retaining means between said second positioning means and an anchor point on said flosser, including said anchor point, wherein said first tension restraining means includes compression means to receive and compress therebetween a strand of dental floss which extends from said storage cavity towards said first positioning means, wherein said compression means includes a frusto-conical projection extending from one of said body portion and head portion, a corresponding recess in the other of said portions having an interior frusto-conical configuration and dimension corresponding to that of said frusto-conical projection, said strand of dental floss passing freely between the outer surface of said frusto-conical projection and the inner surface of said recess when said head portion is loosened from said body portion, said strand of dental floss being tightly compressed between said surfaces when said head portion is tightly secured to said body portion, wherein said frusto-conical projection extends from said body portion and said recess is in said head portion, said frusto-conical projection having a cylindrical base portion adjacent said end of said body portion from which it extends, said cylindrical base portion being of smaller diameter than the corresponding dimension of said body portion, a flat shoulder extending laterally out from said cylindrical base portion of said frusto-conical projection toward the edge of said body portion and annularly around said cylindrical base portion, said cylindrical base portion being externally threaded, a flat cut-away portion of said cylindrical base portion extending longitudinally thereof to provide a passageway for a strand of dental floss between said flat cut-away portion and internal threads of corresponding internally threaded portion of said recess when threadedly engaged therewith, including an internally threaded portion of said recess in said head portion, and an aperture opening in said shoulder adjacent said flat cut-away portion, said aperture communicating with said storage cavity to permit a strand of dental floss to pass therefrom, through said aperture, past said flat cut-away portion of said threaded cylindrical base portion of said frusto-conical projection, and toward said first positioning means.

2. A dental flosser as set forth in claim 1, including an outlet channel leading from said recess and opening to the outer wall of said head, said first and second positioning means including a pair of spaced apart arm members, said outlet channel opening to said outer wall of said head at a location between said spaced apart arm members, to permit a strand of dental floss to extend therethrough from said recess for positioning tautly across the span between the free ends of said spaced apart arm members.

3. A dental flosser as set forth in claim 1, including a sealing member seated in said opening of said outlet channel leading from said recess, said sealing member including a bore therethrough having a diameter substantially corresponding to that of a said strand of dental floss, said sealing member including an elongated body portion having a cross-sectional dimension and configuration to that of said outlet channel for a tight fit therein at the opening thereof to the outer wall of said head, said sealing member sealing said opening and outlet channel against the passage of water.

* * * * *